United States Patent [19]

Archer

[11] Patent Number: 5,760,044

[45] Date of Patent: Jun. 2, 1998

[54] METHOD FOR TREATING COCAINE AND AMPHETAMINE DEPENDENCY

[76] Inventor: Sydney Archer, 52 Wisconsin Ave., Delmar, N.Y. 12052

[21] Appl. No.: 648,546

[22] Filed: May 16, 1996

[51] Int. Cl.$^6$ ............................................... A61K 31/44
[52] U.S. Cl. ................................ 514/282; 514/812
[58] Field of Search ............................. 514/282, 812

[56] References Cited

U.S. PATENT DOCUMENTS 3,372,165   3/1968   Archer.
5,512,578   4/1996   Crain et al. ........................ 514/282

OTHER PUBLICATIONS

Chemical Abstracts AN 1996:2572, Hunes et al, 1995.

Chemical Abstracts AN 1970:119804, White et al, 1969.

Fink et al., "Clinical Status of the Narcotic Antagonists in Opiate Dependence," *Antagonist and Antagonist Action of Narcotic Analgesic Drugs. Proceedings of an International Symposium, Aberdean, Scotland, Jul. 1971*, Baltimore, MD:University Park Press, pp. 266–276 (1993).

Gessner in *Essentials of Pharmacology*, Smith et al., eds., Philadelphia:W.B. Saunders, pp. 506–523 (1995).

*Primary Examiner*—Keith MacMillan
*Attorney, Agent, or Firm*—Nixon, Hargrave, Devans & Doyle

[57] ABSTRACT

The present invention relates to methods for treating cocaine and amphetamine dependency. The method involves administering to the patient an effective amount of a compound having the formula:

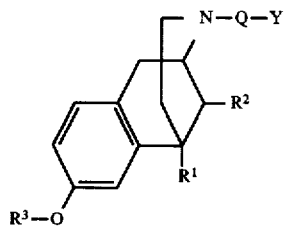

wherein
$R^1$ is selected from the group consisting of hydrogen and C1 to C6 alkyl;

$R^2$ is selected from the group consisting of hydrogen, methyl, and ethyl;

$R^3$ is selected from the group consisting of hydrogen, methyl, C1 to C6 alkanoyl, C3 to C6 cycloalkanoyl, and pyridinecarbonyl;

Q is a bivalent alkylene moiety; and

Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety or a pharmaceutically acceptable acid-addition salt thereof. Discomforting side effects can be minimized by optionally administering naltrexone, naloxone, or a mixture thereof during the early phases of treatment.

24 Claims, 1 Drawing Sheet

FIG. 1

METHOD FOR TREATING COCAINE AND AMPHETAMINE DEPENDENCY

FIELD OF THE INVENTION

The present invention relates to methods for treating cocaine and amphetamine dependency.

BACKGROUND OF THE INVENTION

Cocaine is an alkaloid ester present in the leaves of a shrub that grows at elevations of 2000 to 8000 feet in the Andes Mountains. It can be liberated therefrom by maceration with alkali. From time immemorial this has been accomplished in the Andes by chewing the leaves with lime (calcium carbonate) or ash (source of potassium hydroxide). Cocaine is now produced on an industrial scale in the Andean region of South America and imported into the United States, where its abuse constitutes a major social problem. Amphetamines are synthetic phenylamines with an unsubstituted phenyl ring and ethylamine side chain that has an alkyl substituent on the α carbon, that is, the carbon next to the amine nitrogen. At one time, large-scale diversion of amphetamines to the illicit trade created a widespread abuse problem. This has now been all but supplanted by cocaine abuse. Some of the better known amphetamines include D-amphetamine, methamphetamine, and diethylpropion (TENUATE™, Merrel Dow Pharmaceuticals, Cincinnatti, Ohio).

Both cocaine and amphetamine have high oral availability, although this route of administration results in a 30-minute delay in the onset of action. Accordingly, cocaine abusers resort to intranasal, intravenous, or inhalation routes. The biological half-life of cocaine is short, 0.7–1.5 hours, and its action is mostly terminated by metabolism. The half-life of amphetamine is much longer, 4–20 hours. It is mostly eliminated by urinary excretion, and, because it is a strong base, its half-life is a function of urinary pH. Methamphetamine is more lipid-soluble and enters the brain more rapidly than D-amphetamine, to which it is demethylated.

The reinforcing effects of cocaine and D-amphetamine are very intense and quite similar, and users are unable to distinguish intravenous injections of D-amphetamine from those of cocaine. The intensity and nature of the effects of these agents are very much a function of dose. Low doses make the user feel energetic, clearheaded, and effective as well as wide awake and anorexic. Larger doses cause the user to experience a sense of exhilaration, self-confidence, and power. Athletic performance can be objectively shown to be enhanced. As the dose is increased, the subject comes into a frame of mind dismissive of calamity and danger. Intravenous administration induces a rush, an intense, sensation.

Cocaine and amphetamine have multiple actions on central nervous system ("CNS") monoamine neurotransmitters, namely norepinephrine, dopamine, and serotonin. The reinforcing properties of cocaine are specifically mediated by inhibition of the re-uptake of dopamine. Those of amphetamine are mediated primarily by its enhancement of the release of dopamine from its storage sites. In both instances, this results in higher concentration of dopamine at its post-synaptic receptor as well as at the site of its enzymatic deactivation. Although this produces an enhanced response to dopaminergic stimulation, it also causes depletion of dopamine stores.

Cocaine and amphetamine use results in a number of toxicological effects. Both cocaine and the amphetamines potentiate the peripheral effects of sympathomimetic innervation, causing vasoconstriction. Applied to the nasal mucosa, these agents are therefore effective decongestants. If the vasoconstriction is severe enough, however, ischemia and necrosis follow, resulting in a perforated nasal septum, and at least one instance of a nasal drip of cerebrospinal fluid secondary to a perforation has been reported. Intestinal ischemia secondary to intense mesenteric vasoconstriction can follow ingestion of large doses of cocaine, and, left untreated, it can lead to gangrene. Extreme surges in blood pressure, caused by large parenteral doses, lead to myocardial infarctions, cerebrovascular accidents, ruptured aortas, and abruptio placentae in pregnant women. Other adrenergic effects include marked tachycardia, hyperpyrexia, anxiety, paranoia, and generalized convulsions. Arrhythmias are seen following not only intravenous and inhalation dosing but also intranasal administration in young adults with no pre-existing conditions. Postmortem examination of heart sections indicates the presence of contraction bands. Such bands are known to occur as a consequence of catecholamine-induced cardiac damage and represent a disruption of intracellular calcium homeostasis. Maternal cocaine use can lead to lower than normal fetal birth weight and length for gestational period and smaller head circumference. Maternal cocaine use is also associated with a fourfold greater incidence of congenital malformations and an 8% stillbirth rate owing to abruptio placentae. Chronic cocaine or amphetamine abuse is correlated with toxic paranoid schizophrenia-like reaction characterized by vivid hallucinations (visual, auditory, tactile), paranoid ideation, and changes in affect. All these symptoms occur with a clear sensorium and, if the abuse of the agent is discontinued, resolve in a week or so.

Cocaine and amphetamine use are associated with atypical tolerance phenomena. High-level use is characterized by episodes ("runs") of repetitive self-administration that may last many hours or days. During such periods the user remains continually awake. During a "run", the reinforcing effects of the substance become increasingly attenuated. Some chronic tolerance does build up to the euphoric, cardiovascular, and hyperthermic effects over time, but so does kindling, a phenomenon whereby the threshold for seizures is lowered following repeated cocaine exposure.

Physical dependence to these agents is not as dramatic as in the case of narcotics or depressants. Yet, abrupt cessation of use is followed by symptoms that are reversed when use resumes. Also, typically, the "run" is continued until supplies are exhausted. Monkeys allowed to self-administer cocaine will continue to do so until they die.

The cessation of amphetamine or cocaine use is followed, first, by increased hunger and prolonged sleep and, second, by depression, general fatigue, and a marked increase in rapid eye movement ("REM") sleep. These effects, as well as other characteristics of drug seeking behavior, are reversed by administration of either cocaine or amphetamine and thus have the characteristics of a withdrawal syndrome. On the other hand, the withdrawal does not result in major, grossly observable physiological disruption.

Naturalistic evaluation of psychic symptoms that follow cocaine "runs" has led to conceptualization of a three-phase sequence of post-cocaine abuse abstinence symptoms. The first phase, the crash phase, begins within 15–30 minutes following the last dose of cocaine and lasts from 3 to 6 days. It is heralded by rapidly mounting depression and characterized by anhedonia, insomnia, irritability, anxiety, and suicidal ideation. The craving for cocaine diminishes, and, after 2–5 hours, the individual refuses cocaine even if offered. Gradually, lethargy and somnolence become apparent and eventually lead to a long sleep, occasionally interrupted by bouts of eating. A second phase can last from 1 to 10 weeks. It begins with negligible cocaine craving and near-normal mood and functioning. In due course dysphoria, joylessness, and a perception of intense boredom develop and are accompanied by increasing craving for cocaine, by memories of the reinforcing effects of the drug, by increasing anxiety, and by efforts to arrange for supplies. The third phase follows. The affective state returns to near-normal levels and craving is episodic, but extreme when triggered by environmental clues such as friends who previously shared in cocaine use or the sight of venipuncture. Such episodes suggest conditioned tolerance as the responsible mechanism. This phase can last for months.

Efforts to treat cocaine-dependent individuals with dopamine agonists have been disappointing. Greater success has been achieved by using antidepressants, which are dopamine receptor blockers. Such agents are thought to reverse the supersensitivity induced by stimulant use in a dopaminergic inhibitory autoreceptor. Desipramine is one agent effective in this respect. Administered to cocaine abusers, it significantly reduces both cocaine use and cocaine craving and has been found to remain effective for at least 6 weeks. Its main disadvantage is that the reduction in craving develops slowly over 7–14 days. The long delay in the onset of craving reduction by desipramine poses a problem because, among outpatients, resumption of cocaine use in the interim is frequent. Flupenthixol can also be used to reverse dopaminergic inhibitory autoreceptor supersensitivity. Flupenthixol is a neuroleptic agent and, administered in a depot form, has been reported to decrease cocaine craving and increase retention of patients in treatment. In low doses, it has a rapid antidepressant activity that lasts for 2–4 weeks. It is considered to act by blocking the inhibitory dopamine autoreceptors. None of these drugs are teribbly effective against cocaine abuse.

Cocaine and amphetamine abuse has also been treated by administering ibogamine, an alkaloid of the family apocynaceae, and its derivatives to the abuser (U.S. Pat. No. 4,587,243 to Lotsof). However, in humans, as in rats, ibogaine's efficacy in anti-addictive therapy appears to vary substantially from one individual to another, and at least 30% of treated addicts do not decrease their drug intake. The utility of ibogaine is also limited by several side effects: numbing of the skin; perception of auditory buzzing or oscillating sounds, flashes of light, and the appearance of a vibration to all objects; nausea; and hallucinations. In addition to the stimulant and hallucinogenic side effects, ibogaine induces tremors which appear to be due to activation of an olivo-cerebellar pathway. In rats, high doses of ibogamine have been shown to produce damaged to the cerebellar vermis, presumably a result of overstimulation of cerebellar Purkinje cells.

Like cocaine and amphetamine addiction, addiction to opiates is an important social and medical problem in today's society.

Opiate addiction is sustained by several reinforcing properties. These include feelings of repose, tranquillity, and unconcern, generally known as mood elevation. Another reinforcing property of opiates is an intense "high", an immediate, thrill-like transient sensation, experienced following intravenous administration.

Although the sensations of cocaine, amphetamines, and opiates are in some ways similar, and despite the common, important social consequences which arise from abuse of these three substances, methods for treating cocaine and amphetamine addiction, on the one hand, and opiate addiction, on the other, have diverged. This divergence has become more pronounced as the mechanism of opiate addiction has become better understood.

The reinforcing effects of opiates are mediated by their action on μ receptors, particularly those in the ventral tegmental and nucleus accumbens areas of the brain. To have high affinity for the receptor, opioids related to heroin usually possess a phenolic ring and a piperidine nitrogen. The substituents on the nitrogen determine the intrinsic μ activity of the agent.

The mechanism of physical dependence on opiates most clearly involves the noradrenergic cells of the locus ceruleus. Opiates act as antagonists at the inhibitory μ receptors of these cells, thereby decreasing presynaptic norepinephrine release by the cells. Over time, this results in an up-regulation of postsynaptic norepinephrine receptors. Concurrently, morphine down-regulates the synthesis of β-endorphin, which normally acts at the inhibitory μ receptors. When the opiate is withdrawn, the cell, no longer being inhibited, releases norepinephrine presynaptically. At the same time, the postsynaptic supersensitivity, which results from the increase in norepinephrine receptors, leads to an amplification of the response, and an adrenergic storm ensues.

In response to the understanding of the central role of the μ receptor in the mechanism of opiate addiction, several abstinence-oriented strategies have been developed to treat opiate addiction.

One such abstinence-oriented strategy involves the regular, typically twice weekly, administration of naltrexone, a potent, orally-effective, long-lasting μ-receptor blocking agent.

In another abstinence-oriented treatment, the opiate-dependent individual is maintained on buprenorphine. Because it is a partial μ-receptor agonist, buprenorphine has some slight reinforcing properties, and its acceptability by the opiate-dependent individual is high, as is compliance. At the same time, because it has high affinity for the μ-receptor, it blocks the effects of opiates and causes the opiate-dependent individual to stop seeking them.

Yet another drug used to treat opiate dependence is cyclazocine, an N-substituted benzomorphan derivative. (See Resnick et al., "Cyclazocine Treatment of Opiate Dependence—A Progress Report," *Comprehensive Psychiatry*, 1971:496–501 (1971).) Cyclazocine's binding constant with the μ site (0.24±0.03 nanomoles) and its ineffectiveness in D'Amour-Smith tail-flick tests indicate that cyclazocine's utility in treating opiate dependence arises from its potent μ antagonist activity.

However, since the μ receptor has not been implicated in cocaine and amphetamine addiction, cocaine and amphetamine treatment protocols have not focussed on drugs which interact with μ receptors, such as the ones found useful in the abstinence-oriented treatment of opiate addiction.

In view of the serious health effects of cocaine and amphetamine dependency and the limitations of presently-available methods for treating these addictions, a need remains for effective methods of reducing cocaine and amphetamine addiction. The present invention is directed to meeting this need.

SUMMARY OF THE INVENTION

The present invention relates to methods for treating a patient addicted to cocaine, amphetamine, or both.

In one aspect of the present invention, the method includes administering to the patient an effective amount of a compound having the formula:

wherein
$R^1$ is selected from the group consisting of hydrogen and C1 to C6 alkyl;
$R^2$ is selected from the group consisting of hydrogen, methyl, and ethyl;
$R^3$ is selected from the group consisting of hydrogen, methyl, C1 to C6 alkanoyl, C3 to C6 cycloalkanoyl, and pyridinecarbonyl;
Q is a bivalent alkylene moiety; and
Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety
or a pharmaceutically acceptable salt thereof.

In another aspect of the present invention, the method includes administering to the patient from about 0.05 to about 0.06 mg/kg of the patient's body weight per day of a compound having the formula:

wherein
$R^1$ and $R^2$ are each methyl;
$R^3$ is hydrogen;
Q is methylene; and
Y is cyclopropyl
or a pharmaceutically acceptable salt thereof. The method also includes administering from about 0.6 to about 0.8 mg/kg of the patient's body weight per day of naltrexone to the patient.

Employing the methods of the present invention, cocaine and amphetamine use by a patient dependent on or addicted to cocaine or amphetamines can be reduced. These methods are specific to cocaine and amphetamines, and do not affect motivated consumption of other materials, such as water and food.

DETAILED DESCRIPTION OF THE INVENTION

The present invention relates to methods for treating a patient addicted to cocaine, amphetamine, or both.

In one aspect of the present invention, the method includes administering to the patient a compound having the formula (Formula I):

in an effective amount. These compounds are derivatives of 1,2,3,4,5,6-hexahydro-8-hydroxy-2,6-methano-3-benzazocines and, more particularly, are identified by the generic name 1,2,3,4,5,6-hexahydro-3-(Y—Q—)-6-($R^1$)-11-($R^2$)-8-($R^3$—O—)-2,6-methano-3-benzazocines. In an alternative system of nomenclature, the compounds useful in treating cocaine or amphetamine addiction are designated as benzomorphan derivatives, that is, as 2-(Y—Q—)-2'-($R^3$—O—)-5-($R^1$)-9-($R^2$)-6,7-benzomorphans.

$R^1$ is selected from the group consisting of hydrogen and C1 to C6 alkyls. Suitable C1 to C6 alkyls are those containing from 1 to 6 carbon atoms, including linear and branched C1 to C6 alkyls, such as methyl, ethyl, n-propyl, iso-propyl, n-butyl, 1-methylpropyl, 2-methylpropyl, tert-butyl, pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1-ethyl-1-methylpropyl, and 1-ethyl-2-methylpropyl. The C1 to C6 alkyl can also be or include a cyclic alkyl group, such as cyclopropyl, cyclobutyl, cyclopentyl, and cyclohexyl. When $R^1$ is a C1 to C6 alkyl, it preferably contains from 1 to 4 carbon atoms.

$R^2$ is selected from the group consisting of hydrogen, methyl, and ethyl.

$R^3$ is selected from the group consisting of hydrogen, methyl, C1 to C6 alkanoyl, C3 to C6 cycloalkanoyl, and pyridinecarbonyl. Suitable C1 to C6 alkanoyl groups are those containing 1–6 carbon atoms, including, for example, formyl, acetyl, propionyl, butyroyl, isobutyroyl, and caproyl. When $R^3$ is pyridinecarbonyl, it can be 2-pyridinecarbonyl or picolinoyl, 3-pyridinecarbonyl or nicotinoyl, and 4-pyridine-carbonyl or isonicotinoyl. Suitable C3 to C6 cycloalkanoyl moieties include cyclopropanoyl, cyclobutanoyl, cyclopentanoyl, and cyclohexanoyl.

Q is a bivalent alkylene moiety. These bivalent alkylene moiety can be branched or unbranched, and, preferably, are saturated hydrocarbon radicals having 1–4 carbons. Illustrative examples of suitable bivalent alkylene moieties are
—$CH_2$—, —$CH(CH_3)$—, —$C(CH_3)_2$—, —$CH(CH_2CH_3)$—, —$CH_2CH_2$—, —$CH(CH_3)CH_2$—, —$C(CH_3)_2CH_2$—, —$CH(CH_3)CH(CH_3)$—, —$CH_2CH_2CH_2$—, —$CH_2$—$CH(CH_3)$—$CH_2$—, —$CH(CH_3)$—$CH_2$—$CH_2$—, —$CH_2CH_2CH_2CH_2$—, and the like.

Y can be a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety.

Suitable cycloalkyl moieties include cyclopropyl, cyclobutyl, cyclopentyl, cyclohexyl, cycloheptyl, and the like. Although it is preferred that the cycloalkyl moiety be unsubstituted, compounds containing substituted alkyl moieties, such as 3,3-dimethylcyclobutyl, and 3-methylcyclopentyl, are suitable for use in the practice of the present invention.

Halo-(C2 to C6)-alkenyl moieties include monovalent unsaturated halo-hydrocarbon radicals having 1 chlorine or bromine atom, 2 chlorine atoms, 2 bromine atoms, or 1 bromine and 1 chlorine atom attached to the ethylenic carbon atoms, that is, to those carbon atoms involved in the carbon-carbon double bond. For example, the halo-(C2 to C6)-alkenyl moieties can have the formula —$CX^1$=$CX^2X^3$, where one or two of $X^1$, $X^2$, and $X^3$ are independently selected from the group consisting of bromine and chlorine, and the remaining of $X^1$, $X^2$, and $X^3$ are hydrogen, such as —CH=CHCl, —CH=CHBr, —CCl=$CH_2$, —CBr=$CH_2$, —CH=$CCl_2$, —CH=CClBr, —CH=$CBr_2$, —CCl=CHCl, —CBr=CHBr, —CBr=CHCl, and —CCl=CHBr. Other suitable halo-(C2 to C6)-alkenyl moieties include —$CH_2$—CH=CHCl, —$CH_2$—CH=$CCl_2$, —$CH_2$—CH=$CBr_2$, —$CH_2$—CCl=$CH_2$, —$CH_2$—CCl=CHCl, —$CH_2$—CH=CHCl, —CH=CCl—$CH_3$, —$CH_2$—$CH_2$—CH=CHCl, —$CH_2$—CCl=CH—$CH_3$, —$CH_2$—CH=CCl—$CH_3$, —$CH_2$—CBr=CH—$CH_3$, —$CH_2$—CH=CBr—$CH_3$, —$CH_2$—CCl=CCl—$CH_3$, —$CH_2$—CBr=CBr—$CH_3$, —$CH_2$—CCl=CBr—$CH_3$, —$CH_2$—CBr=CCl—$CH_3$, —CCl=C($CH_3$)$_2$, —CBr=C($CH_3$)$_2$, —C($CH_3$)=CHCl, —C($CH_3$)=$CCl_2$, —C($CH_3$)=CClBr, —C($CH_3$)=$CBr_2$, —CH=CCl—$CH_2$—$CH_3$, —$CH_2$—$CH_2$—$CH_2$—CH=CHCl, —$CH_2$—$CH_2$—CH=CCl—$CH_3$, —$CH_2$—CH=CCl—$CH_2$—$CH_3$, —CH=CCl—$CH_2$—$CH_2$—$CH_3$, —$CH_2$—$CH_2$—$CH_2$—CH=CHCl, —$CH_2$—$CH_2$—$CH_2$—CH=CCl—$CH_3$, —$CH_2$—$CH_2$—CH=CCl—$CH_2$—$CH_3$, —$CH_2$—CCl=CBr—$CH_2$—$CH_2$—$CH_3$, and —CH=CBr—$CH_2$—$CH_2$—$CH_3$.

Cyano-(C3 to C6)-alkenyl moieties include monovalent unsaturated cyano-hydrocarbon radicals having a double bond and at least one, preferably one or two, cyano groups, such as —CH=CH(CN), —C(CN)=$CH_2$, —C($CH_3$)=CH(CN), —$CH_2$—CH=CH(CN), —$CH_2$—$CH_2$—CH=CH(CN), —CH=CH—$CH_2$—$CH_2$—$CH_2$(CN), and —CH=C(CN)$_2$.

Particularly preferred compounds for use in the practice of the present invention are those where Y is cyclopropyl. More preferably, Q is methylene, $R^1$ and $R^2$ are each methyl, and $R^3$ is hydrogen. Most preferably, the compound used in the practice of the present invention is cyclazocine, 1,2,3,4,5,6-hexahydro-3-cyclopylmethyl-6,11-dimethyl-8-hydroxy-2,6-methano-3-benzocyanine.

The above described compounds can exist in stereochemically isomeric forms, that is, optical isomers and geometric isomers. Compounds suitable for administration in accordance with this invention include pure optical and geometric isomers or mixtures of these optical and geometric isomers. If desired, the isolation or the production of a particular stereochemical form can be accomplished by application of the general principles known in the prior art.

The method of the present invention may also be practiced using acid-addition salts, preferably pharmaceutically acceptable acid-addition salts, of the compounds of Formula I, either in addition to or in place of the compounds of Formula I. The acid-addition salt forms of these compounds are structurally the same as the compounds of Formula I, except that the cation (generally the proton) of the acid used in their preparation is bonded to the nitrogen, imparting a positive charge thereto, and that the anion of the acid used is present to balance the charge.

These acid-addition salts are prepared from any organic acid; inorganic acid, including organic acids having an inorganic group therein; organo-metallic acid, as exemplified by organic mono- and poly-carboxylic acids, such as those found, for example, in *Beilstein's Organische Chemie*, 4th ed., Volumes III, IV, IX, X, XIV, XVII, XIX, XXI, XXII, and XXV, which are hereby incorporated by reference; organic mono- or poly-sulfonic acids or sulfinic acids, such as those found, for example, in *Beilstein's Organische Chemie*, 4th ed., Volumes VI, XI, XVI, and XXII, which are hereby incorporated by reference; organic phosphonic or phosphinic acids, such as those found, for example, in *Beilstein's Organische Chemie*, 4th ed., Volume XVI, which is hereby incorporated by reference; organic heterocyclic carboxylic, sulfonic, or sulfinic acids, such as those found, for example, in *Beilstein's Organische Chemie*, 4th ed., Volumes XVIII, XXII, and XXV, which are hereby incorporated by reference; acidic ion-exchange resins; or inorganic acids of any acid forming element or combination of elements such as those described in Mellor, *Comprehensive Treatise on Inorganic and Theoretical Chemistry*, Volumes I-XVI, New York: Longman's, Green and Co., which are hereby incorporated by reference. In addition, other salt-forming compounds which are acidic in their chemical properties but which are not generally considered as acids in the same sense as carboxylic or sulfonic acids can be used to prepare the acid-addition salt forms of the compounds useful in practicing this invention. Thus, there are also included acidic phenolic compounds, such as those found, for example, in Volume VI of *Beilstein's Organische Chemie*, 4th ed., which is hereby incorporated by reference, and acidic compounds having "activated" or acidic hydrogen atoms, such as those found, for example, in Cox et al., *Medicinal Chemistry*, Vol. IV, New York: John Wiley and Sons, Inc. (1959), which is hereby incorporated by reference.

Representative acids for the formation of the acid-addition salts include formic acid, acetic acid, isobutyric acid, alpha-mercaptopropionic acid, trifluoroacetic acid, maleic acid, fumaric acid, succinic acid, succinamic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, and the like. The acid-addition salts with lactic acid and with ethanesulfonic acid, for example, are water-soluble and are especially suitable forms for practicing the present invention.

The acid-addition salts are prepared in conventional fashion, for instance, by direct mixing of the acid and the free base of the compounds having the structure of Formula I or their isoelectric forms. When this is not appropriate, acid-addition salt preparation can be effected by dissolving either or both the acid and the free base or isoelectric form separately in water or in an organic solvent and mixing the two solutions or by dissolving both the acid and the free base or isoelectric form together in a solvent. The resulting acid-addition salt is isolated by filtration, if it is insoluble in the reaction medium, or by evaporation of the reaction medium to leave the acid-addition salt as a residue. The acid moieties or anions in the salt forms of the compounds of Formula I are not critical and, therefore, can be any acid anion or acid-like substance capable of salt formation with the free base or isoelectric forms of these compounds.

The method of the present invention can be used to treat a patient who is addicted to cocaine alone, amphetamine alone, or both cocaine and amphetamine.

As used herein cocaine is meant to include the naturally occurring alkaloid ester and the pharmaceutically active derivatives thereof. One class of such pharmaceutically active derivatives is the acid addition salts of the naturally occurring alkaloid ester, examples of which include cocaine nitrate, cocaine sulfate, and, paricularly, cocaine hydrochloride, commonly referred to as "crystal" or "snow". Pharmaceutically active derivatives of the alkaloid ester also include the organic solvent (particularly the ether) extract residue of cocaine acid addition salts (particularly cocaine hydrochloride) treated with strong base such as alkali metal hydroxides, commonly referred to as "free base", and the reaction product of cocaine acid addition salts (particularly cocaine hydrochloride) and bicarbonate, commonly referred to as "crack". Other pharmaceutically active cocaine derivatives, treatment of the addiction to which is contemplated by the present invention, include the N-ethyl congener of cocaine (i.e. cocaethylene) as well as other 3-(benzoyoxy)-8-alkyl-8-azabicyclo[3.2.1]octane-2-carboxylic acid alkyl and aryl esters, carboxylic acids, carboxylic acid salts, carboxylic acid amides, and their acid addition salts.

Amphetamine, as used herein, refers to the class of phenylamines which have an unsubstituted phenyl ring bearing an ethylamine side chain that has an alkyl substituent on the carbon $\alpha$ to the carbon to which amine nitrogen is bonded. Examples of amphetamines include the compound for which the class is named, amphetamine ($\alpha$-methylbenzethanamine), its optically pure d-form, its optically pure l-form, its optically pure dl-form, racemic mixtures of its d-, l-, and dl-forms, amphetamine phosphate, amphetamine succinate, methamphetamine, benzphetamine, phentermine, diethylpropion, phenmetrazine, phendimetrazine, chlorphentermine, clortermine, mazindol, phenylpropanolamine, and methylphenidate. Other examples of amphetamine, addiction to which can be treated with the methods of the present invention, are described in O'Brien et al. in *Goodman and Gilman's The Pharmacological Basis of Therapeutics*, Hardman and Limbird, eds., 9th ed., p.571 (1996), which is hereby incorporated by reference.

As used herein, "addicted to" and "addiction to" a substance (and other forms of this phrase) means a habitual or recurrent use of the substance. It is meant to include, but is not meant to be limited to, a dependency on the substance. Dependency is characterized by a patient's persistence in substance use or abuse or the recurrence of such use or abuse in the face of negative social or medical consequences of this use or abuse or in face of the patient's declared or undeclared intent to abandon or reduce his or her use of the substance. A patient's dependency can be manifested in objective criteria or other indicies of drug seeking behavior, such as repeated attempts to abandon use or abuse of the substance, as evidenced by, for example, past participation in encounter groups designed to reduce the participants' use of cocaine or amphetamine, commitment to a cocaine or amphetamine rehabilitation program, arrest or conviction of cocaine or amphetamine possession or trafficking, hospitalization for complications arising from cocaine or amphetamine use, including overdose, and the like.

Patient, as used herein, is generally meant to be a human. However, it is envisioned that the method of the present invention can be used to treat cocaine, amphetamine, or both cocaine and amphetamine addiction in experimental mammals other than humans, such as primates other than humans, rats, mice, dogs, and the like. Using the methods of the present invention, mammals experimentally addicted to cocaine or amphetamine or both can be humanely weaned from the substance, and the physiological and phsycological damage or changes which result from past cocaine use or abuse can be assessed. In addition, these mammals can be used to study the progression of or recovery from such physiological and psychological damage or changes subsequent to the patient's abandoning or reducing his, her, or its cocaine or amphetamine use. In the controlled environment of the laboratory, the non-human mammalian patient would be allowed to develop a cocaine, amphetamine, or both a cocaine and amphetamine addiction and to maintain this addiction for a prescribed period of time. The patient's addiction would then be treated in accordance with the method of the present invention to cause the patient's use of the drug to decrease or cease. The patient could then be monitored over time from the time of drug use cessation or reduction to ascertain long-term physiological or psychological changes or damage and the patient's recovery from these changes or damage.

Treatment, in accordance with the present invention, includes administering to the patient an effective amount of a compound according to Formula I or a pharmaceutically acceptable salt thereof.

It will be appreciated that the actual preferred effective amount of compound will vary according to the particular compound, the particular composition formulated, and the mode of administration. Many factors that modify the compound's activity will be taken into account by those skilled in the art; e.g., body weight, sex, diet, time of administration, route of administration, rate of excretion, condition of the patient, drug combinations, reaction sensitivities and severities, severity of addiction, and the stage at which the patient is in the withdrawl process. Administration can be carried out continuously or periodically within the maximum tolerated dose.

Preferably, the compound is administered in an amount from about 0.025 to about 0.56 mg/kg of the patient's body weight per day, more preferably, in an amount from about 0.05 to about 0.12 mg/kg of the patient's body weight per day. The optimal daily dose for a particular patient can be determined by challenging the patient with a dose of cocaine or amphetamine. The optimal daily dose of compound is the minimal dose at which the patient does not feel the effects of the challenge dose.

The amount can be administered in a single daily dose or in multiple doses or even continuously. Continuous administration can be carried out in the inpatient setting by, for example, intravenous drip, or in an outpatient setting by providing the compound in a slow-release formulation, such as in a suspension or in microcapsules. In the outpatient setting, the administering is best carried out continuously in a slow release formulation, or, alternatively, in a single dose. In either case, to ensure compliance with the treatment protocol, it is best that the provider actively administer (i.e. inject, etc.) each individual dose to the patient or, otherwise, that the provider observe the patient self-administer each dose.

Although some cocaine or amphetamine addiction treatment is effected with the first dose of the compound subsequent to cessation, multiple doses given over more than one day are preferred. Preferably, treatment is conducted for at least four days, more preferably for at least four consecutive days, more preferably, for at least the first consecutive four days following cessation. The daily dose during the four days can be constant, or it can vary from day to day. Preferably, the patient is started on a low daily dose, which is gradually increased, preferably over the course of four days, so that on the fourth and subsequent days, the patient is receiving the preferred daily dose indicated above (referred to hereinafter as the "maintenance dose"). In such a treatment protocol, the compound is administered in an amount from about 0.00625 to about 0.14 mg/kg of the patient's body weight per day on the first day of treatment, in an amount from about 0.0125 to about 0.28 mg/kg of the patient's body weight per day on the second day of treatment, in an amount from about 0.01875 to about 0.42 mg/kg of the patient's body weight per day on the third day of treatment, and in an amount from about 0.025 to about 0.56 mg/kg of the patient's body weight per day on the fourth and subsequent days of treatment. More preferably, the amounts of compound administered on the first, second, third, and fourth and subsequent days are from about 0.0125 to about 0.03 mg, from about 0.025 to about 0.06 mg, from about 0.0375 to about 0.09 mg, and from about 0.05 to about 0.12 mg, respectively, per kilogram of the patient's body weight per day.

It is especially preferred that the daily dose be, on the first day, one-quarter the maintenance dose; on the second day, one-half the maintenance dose; on the third day, three-quarters the maintenance dose; and on the fourth and subsequent days, the full maintenance dose.

Optimal administration amounts and rates for a given patient under a given set of conditions can be ascertained by those skilled in the art using conventional dosage administration tests in view of the above guidelines.

The compound can be administered by any of the conventional modes of drug administration, including oral or parenteral administration. Examples of parenteral administration are intraventricular, intracerebral, intramuscular, intravenous, intraperitoneal, rectal, and subcutaneous administration.

The compounds of the present invention may be administered alone or in combination with suitable pharmaceutical carriers or diluents. The diluent or carrier ingredients should be selected so that they do not diminish the therapeutic effects of the compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology*, 3rd edition, volume 15, New York: John Wiley and Sons, pp. 470–493 (1981), which is hereby incorporated by reference.

Administration of the compound in accordance with the present invention frequently leads to discomforting side effects, especially during the first four days of treatment. It has been found that these discomforting side effects can be minimized by administering naloxone (4,5-epoxy-3,14-dihydroxy-17-(2-propenyl)morphinan-6-one) or, preferably, naltrexone (17-(cyclopropylmethyl)-4,5-epoxy-3,14-dihydroxymorphinan-6-one) during the period of time when discomforting side effects of the compounds are present, generally during the first four days of treatment, in an amount effective to reduce the compound's side effects. Naltrexone or naloxone administration is usually discontinued when the daily dose of compound equals the optimal or maintenance dose. Mixtures of naloxone and naltrexone can also be used.

Naltrexone or naloxone can be coadministered with the compound of the present invention, such as in a single oral dosage form containing both the compound and naltrexone or naloxone. Alternatively, the naltrexone or naloxone can be administered separately from the compound in any suitable dosage form, as discussed above, and this dosage form can be the same as or different from the dosage form of the compound. Naltrexone or naloxone can be administered alone or in combination with suitable pharmaceutical carriers or diluents, the selection of which depends on the mode of administration, as will be appreciated by those skilled in the art.

The amount of naltrexone or naloxone and the frequency of administration will vary depending on the particular composition formulated and the mode of administration. Many factors that modify the activity of naltrexone or naloxone in reducing discomforting side effects will be taken into account by those skilled in the art, including body weight, sex, diet, time of administration, route of administration, rate of excretion, condition of the patient, drug combinations, and reaction sensitivities and severities. In many cases, naltrexone or naloxone will be administered as requested by the patient. Administration of naltrexone or naloxone can be carried out continuously or periodically within the maximum tolerated dose.

Naltrexone or naloxone is administered, preferably, in an amount from about 0.07 to about 7 mg/kg of the patient's body weight per day and, more preferably in an amount from about 0.6 to about 0.8 mg/kg of the patient's body weight per day.

The 1,2,3,4,5,6-hexahydro-3-(Y—Q—)-6-($R^1$)-11-($R^2$)-8-hydroxy-2,6-methano-3-benzazocine compounds employed in the practice of the present invention can be prepared by any suitable method. One convenient method is described in U.S. Pat. No. 3,372,165 to Archer et al., which is hereby incorporated by reference.

Briefly, 1,2,3,4,5,6-hexahydro-3-(Y—Q—)-6-($R^1$)-11-($R^2$)-8-hydroxy-2,6-methano-3-benzazocine compounds are prepared in their isoelectric forms by N-alkylating the corresponding amines, namely the 1,2,3,4,5,6-hexahydro-6-($R^1$)-11-($R^2$)-8-hydroxy-2,6-methano-3-benzazocines, by heating with an alkylating agent having the formula Y—Q—M where Q and Y have the same meaning indicated above and M is the anion, such as sodium or potassium anion, of a strong organic or inorganic acid, such as an alkali metal carbonate or bicarbonate. This alkylation reaction is preferably carried out in the presence of a suitable reaction medium, such as a lower alkanol, for instance methanol or ethanol, or an N,N-(di-lower alkyl)-lower alkanamide, for instance, N,N-dimethylformamide or N,N-dimethylacetamide.

Where the 8-methoxy or 8-acyloxy forms of the compound are desired they can be conveniently obtained by appropriate etherification or esterification, respectively, of the corresponding 8-hydroxy compounds, using any of the conventional prior art methods suitable for the etherification or esterification of phenols.

For instance, 8-methoxy compounds of Formula I are obtained directly by treatment of the 8-hydroxy compounds of Formula I with diazomethane. Alternatively, 8-methoxy compounds of Formula I are obtained by treatment of the 8-hydroxy compounds of Formula II, hereinbelow, with diazomethane or with dimethyl sulfate to produce the 8-methoxy compounds of Formula II. The latter compounds are reduced with lithium aluminum hydride to produce the 8-methoxy compounds of Formula I.

Treatment of the 8-hydroxy compounds of Formula I with an acid anhydride (having the formula $(R^3CO)_2O$) or acid chloride (having the formula $R^3COCl$) of a C1 to C6 alkanoic acid or pyridinecarboxylic acid yields the corresponding 8-(C1 to C6 alkanoyloxy) or 8-(pyridinecarboyloxy) compounds of Formula I.

Another method suitable for preparing 1,2,3,4,5,6-hexahydro-3-(Y—Q—)-6-($R^1$)-11-($R^2$)-8-(hydroxy or methoxy)-2,6-methano-3-benzazocines wherein Q has a —$CH_2$— moiety at its linkage to the nitrogen atom, comprises N-acylating a 1,2,3,4,5,6-hexahydro-6-($R^1$)-11-($R^2$)-8-(hydroxy or methoxy)-2,6-methano-3-benzazocine with one or two molecular equivalents of an acid halide or acid anhydride of an acid having the formula Y—Q'—COOH where —Q'— is selected so that —Q— can be represented by —Q'—$CH_2$—. The resulting amide or ester-amide derivative is a 1,2,3,4,5,6-hexahydro-3-(Y—Q'—C(O)—)-6-($R^1$)-11-($R^2$)-8-hydroxy or methoxy-2,6-methano-3-benzazocine having the structural formula (Formula II):

When one molecular equivalent of the acylating agent is used, Z is hydrogen when $R^3$ in the starting benzazocine is hydrogen and Z is $R^3$ when $R^3$ in the starting benzazocine is other than hydrogen. When $R^3$ in the starting benzazocine is hydrogen and two molecular equivalents of the acylating agent are used, Z in the product is Y—Q'—C(O)—.

The resulting amide or ester-amide derivative is converted to a compound useful in the practice of the present invention by treating the compound of Formula II with a reducing agent, such as lithium aluminum hydride. This reducing agent is effective to reduce the carbonyl of the amide group to a methylene, —$CH_2$—, thereby converting the Y—Q'—C(O)— moiety of Formula II to the Y—Q— moiety of Formula I without affecting any ethylenic linkages. In the N-acylation of the 8-hydroxy compounds of Formula II, in some instances, both N- and O-acylation may occur, yielding a mixture of the 3-acyl and 3-acyl-8-acyloxy compounds. However, this is of no consequence in the over-all process, because, in the reduction step, both the amides (Z=H or alkyl) and the ester-amides (Z=acyl) of Formula II are converted to the 1,2,3,4,5,6-hexahydro-3-(Y—Q—)-6-($R^1$)-11-($R^2$)-8-hydroxy-2,6-methano-3-benzazocine where Q is unbranched at its linkage to the nitrogen atom.

The 1,2,3,4,5,6-hexahydro-6-($R^1$)-11-($R^2$)-8-hydroxy-2,6-methano-3-benzazocine starting materials used in preparing the compounds useful in the practice of this invention can be obtained by application of known procedures. For example, a 3-($R^2$)-4-($R^1$)-pyridine methiodide is interacted with p-methoxybenzylmagnesium chloride; the resulting N-methyl-2-(p-methoxybenzyl)-3-($R^1$)-4-($R^2$)-1,2-dihydropyridine is reduced with sodium borohydride or by catalytic hydrogenation to produce an N-methyl-2-(p-methoxybenzyl)-3-($R^2$)-4-($R^1$)-1,2,5,6-tetrahydro-pyridine; and this latter product is heated with an appropriate cyclizing agent, such as concentrated hydrobromic or phosphoric acid, to yield a 1,2,3,4,5,6-hexahydro-3-methyl-6-($R^1$)-11-($R^2$)-8-hydroxy-2,6-methano-3-benzazocine. By acetylating the 8-hydroxyl group in this cyclization product, such as by treatment with acetic anhydride, and treating the resulting 8-acetoxy compound with cyanogen bromide, there is produced a 1,2,3,4,5,6-hexahydro-3-cyano-6-($R^1$)-11-($R^2$)-8-acetoxy-2,6-methano-3-benzazocine which, by heating with dilute hydrochloric acid, is converted to the desired 1,2,3,4,5,6-hexahydro-6-($R^1$)-11-($R^2$)-8-hydroxy-2,6-methano-3-benzazocine. This series of reactions is illustrated in Examples 1–4.

The alkylating agents Y—Q—M used in the alkylation procedure for preparing compounds useful in the practice of the present invention are likewise readily obtainable by known procedures. For example, in one method, the corresponding alcohol having the formula Y—Q—OH is esterified with a strong organic or inorganic acid having the formula H—M.

Naltrexone is available commercially. Alternatively, it can be prepared by a variety of methods known in the art, such as those described in U.S. Pat. No. 4,795,813 to Schwartz and U.S. Pat. No. 3,332,950 to Blumberg et al., which are hereby incorporated by reference. Naloxone can also be prepared by known methods, such as those described in U.S. Pat. No. 3,254,088 to Lewenstein et al., which are hereby incorporated by reference.

The present invention is further illustrated by the following examples.

EXAMPLES

Example 1

Subjects and Apparatus

The subjects were naive female Sprague-Dawley rats approximately 3 months old weighing 230–250 grams at the beginning of the experiment; female rats were used because they grow at a much slower rate than males and are less likely than males to outgrow their intravenous cannulas. Rats were housed singly in Wahmann hanging cages (Wahmann Mfg. Co., Timonium, Md.) and maintained on a normal light/dark cycle. All self-administration testing was conducted in twelve BRS/LVE operant test cages, each enclosed in a sound-attenuated cubicle. Responses on either of two levers were recorded on an IBM compatible 386 computer with a Med Associates Inc. interface. The intravenous self-administration system consisted of polyethylene-silicone cannulas according to the design of Weeks in *Methods in Psychobiology, Vol. 2*, Myers, ed., New York: Academic Press, pp. 155–168 (1972)("Weeks"), which is hereby incorporated by reference.

Example 2
Treatment of Cocaine-Addicted Rats with Cyclazocine

Shaping of the bar-press response was initially accomplished by training rats to bar-press for water. Cannulas were then implanted in the external jugular vein according to the procedures of Weeks, which is hereby incorporated by reference. Self-administration testing began with a single 24-hour session, 5 days a week. Rats were tested about the same time each day, during the middle of the light cycle. Depending on the group, a lever-press response produced 50 µl infusion of the cocaine solution. Since all rats weighed 250±20 g, each response delivered approximately 0.4 gram of cocaine per kilogram of rat body weight. These doses are about 2–4 times the threshold doses required for maintaining self-administration behavior. One non-contingent drug infusion was administered at the beginning of each session. Experiments to assess the effects of 1,2,3,4,5,6-hexahydro-3-cyclopropylmethyl-6,11-dimethyl-8-hydroxy-2,6-methano-3-benzazocine, commonly referred to as cyclazocine, were begun when baseline self-administration rates stabilized, usually after 2 weeks of testing. To prevent clogging, cannulas were filled with heparin after each use. When blood could not be withdrawn, cannulas were tested by infusing 10 mg/kg of methohexital. If the cannulas were patent the rat would become ataxic immediately.

In order to provide an indication of the specificity of cyclazocine on drug self-administration, cyclazocine's effects on pressing for 0.01 ml of water were assessed in other groups of rats. The operant chambers, reinforcement schedule, and session duration were the same as those used for drug self-administration study. The rats were maintained on a 23 h water deprivation schedule.

Figure 1:
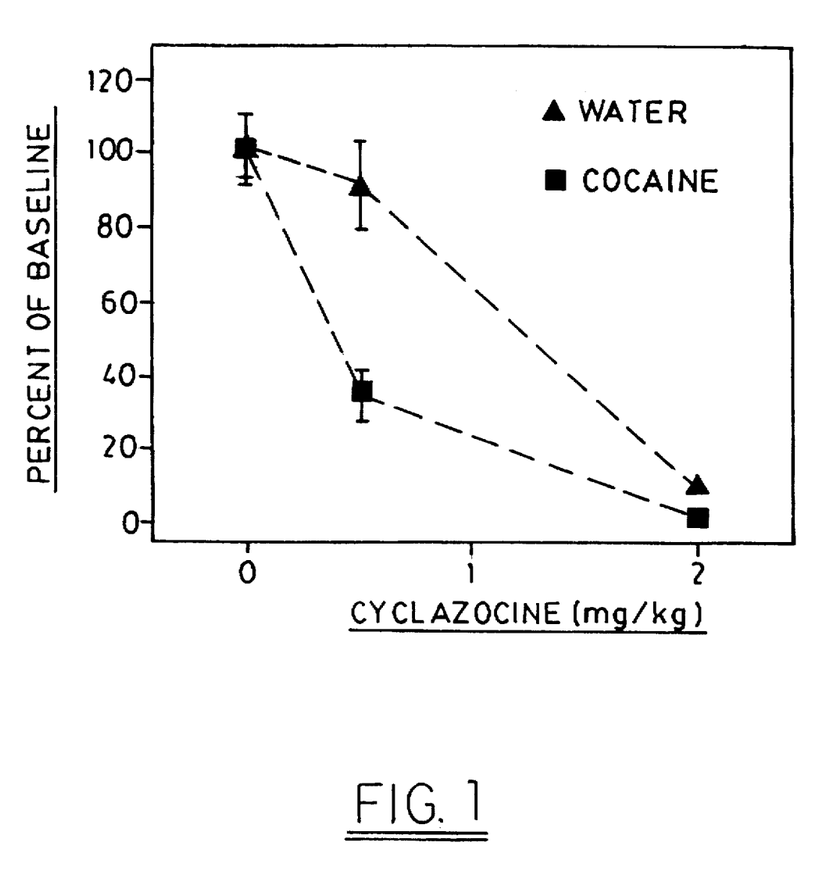
FIG. 1 is a dose-response graph showing the dependence of cocaine and water self-administration on cyclazocine dose.

The effect of cyclazocine doses ranging from 0 to 2 mg/kg on cocaine self-administration (■) and on water intake (Δ) are shown in FIG. 1. As FIG. 1 shows, at a dose of 0.5 mg/kg, the drug reduced cocaine self-administration by over 60% of control without having an effect on water consumption. This effect lasted over 48 hours. No toxic effects and no central nervous system depressant activity was observed.

Example 3
Treatment of Cocaine Addicts with Cyclazocine and Naltrexone

A white male, addicted to cocaine but not a user of opiates, as evidenced by the fact that his urine tests negative for opiates, is given 1.0 mg of cyclazocine along with 50 mg of naltrexone to minimize any discomforting side effects. On the second day the dose of cyclazocine is increased to 2.0 mg, and the same dose of naltrexone is administered. The cyclazocine dose is increased by 1.0 mg increments each day until a maintenance dose of 4.0 mg or somewhat higher is reached. Cocaine challenges are periodically conducted to determine the proper cyclazocine maintenance dose. The proper maintenance dose is that dose of cyclazocine at which the subject no longer feels the challenge dose's effects. The daily dose of cyclazocine is maintained for several months until the patient is dependence-free.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for treating addiction to cocaine, amphetamine, or both in a patient, said method comprising:
   administering to the patient an effective amount of a compound having the formula:

wherein $R^1$ is selected from the group consisting of hydrogen and C1 to C6 alkyl;

$R^2$ is selected from the group consisting of hydrogen, methyl, and ethyl;

$R^3$ is selected from the group consisting of hydrogen, methyl, C1 to C6 alkanoyl, C3 to C6 cycloalkanoyl, and pyridinecarbonyl;

Q is a bivalent alkylene moiety; and

Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety or a pharmaceutically acceptable salt thereof.

2. A method according to claim 1, wherein Y is cyclopropyl.

3. A method according to claim 2, wherein Q is methylene, $R^1$ and $R^2$ are each methyl, and $R^3$ is hydrogen.

4. A method according to claim 1, wherein Y is a cyano moiety or a cyano-(C3 to C6)-alkenyl moiety.

5. A method according to claim 4, wherein Q is methylene, $R^1$ and $R^2$ are each methyl, and $R^3$ is hydrogen.

6. A method according to claim 1, wherein Y is a —$CX^1$=$CX^2X^3$ moiety, one or two of $X^1$, $X^2$, and $X^3$ are independently selected from the group consisting of bromine and chlorine, and the remaining of $X^1$, $X^2$, and $X^3$ are hydrogen.

7. A method according to claim 6, wherein Q is methylene, $R^1$ and $R^2$ are each methyl, and $R^3$ is hydrogen.

8. A method according to claim 1, wherein the compound is contained in a slow-release microcapsule or suspension formulation.

9. A method according to claim 1, wherein the compound is administered orally.

10. A method according to claim 9, wherein the compound is in a tablet, capsule, granular, dispersible powder, suspension, syrup, or elixir form.

11. A method according to claim 10, wherein the compound is in a tablet or capsule form and is admixed with inert diluent, a granulating agent, a disintegrating agent, a lubricating agent, or combinations thereof.

12. A method according to claim 1, wherein the compound is administered in an amount from about 0.025 to about 0.56 mg/kg of the patient's body weight per day.

13. A method according to claim 10, wherein the compound is administered in an amount from about 0.05 to about 0.12 mg/kg of the patient's body weight per day.

14. A method according to claim 1, wherein said treating is carried out for at least four days and wherein a maintenance dose is administered on the fourth and subsequent days of treatment, about three-quarters of the maintenance dose is administered on the third day of treatment, about one-half of the maintenance dose is administered on the second day of treatment, and about one-quarter of the maintenance dose is administered on the first day of treatment, wherein the maintenance dose is from about 0.025 to about 0.56 mg/kg of the patient's body weight per day.

15. A method according to claim 1, wherein said treating is carried out for at least four days and wherein the compound is administered in an amount from about 0.00625 to about 0.14 mg/kg of the patient's body weight per day on the first day of treatment, in an amount from about 0.0125 to about 0.28 mg/kg of the patient's body weight per day on the second day of treatment, in an amount from about 0.01875 to about 0.42 mg/kg of the patient's body weight per day on the third day of treatment, and in an amount from about 0.025 to about 0.56 mg/kg of the patient's body weight per day on the fourth and subsequent days of treatment.

16. A method according to claim 15, further comprising:

administering naltrexone, naloxone, or a mixture thereof to the patient in an amount effective to reduce the compound's side effects during one or more of the first, second, third, and fourth days of treatment.

17. A method according to claim 15, wherein the compound is administered in an amount from about 0.0125 to about 0.03 mg/kg of the patient's body weight per day on the first day of treatment, in an amount from about 0.025 to about 0.06 mg/kg of the patient's body weight per day on the second day of treatment, in an amount from about 0.0375 to about 0.09 mg/kg of the patient's body weight per day on the third day of treatment, and in an amount from about 0.05 to about 0.12 mg/kg of the patient's body weight per day on the fourth and subsequent days of treatment.

18. A method according to claim 17, further comprising:

administering naltrexone, naloxone, or a mixture thereof to the patient in an amount effective to reduce the compound's side effects during one or more of the first, second, third, and fourth days of treatment.

19. A method according to claim 1, further comprising:

administering naltrexone, naloxone, or a mixture thereof to the patient in an amount effective to reduce the compound's side effects.

20. A method according to claim 19, wherein naltrexone, naloxone, or a mixture thereof is coadministered with the compound.

21. A method according to claim 19, wherein naltrexone, naloxone, or a mixture thereof is administered in an amount from about 0.07 to about 7 mg/kg of the patient's body weight per day.

22. A method according to claim 21, wherein naltrexone, naloxone, or a mixture thereof is administered in an amount from about 0.6 to about 0.8 mg/kg of the patient's body weight per day.

23. A method for treating addiction to cocaine, amphetamine, or both in a patient, said method comprising:

administering to the patient from about 0.05 to about 0.12 mg/kg of the patient's body weight per day of a compound having the formula:

wherein $R^1$ and $R^2$ are each methyl;

$R^3$ is hydrogen;

Q is methylene; and

Y is cyclopropyl or a pharmaceutically acceptable salt thereof and administering from about 0.6 to about 0.8 mg/kg of the patient's body weight per day of naltrexone, naloxone, or a mixture thereof to the patient.

24. A method according to claim 23, wherein the compound is contained in a slow-release microcapsule or suspension formulation.

* * * * *